United States Patent [19]

Elias

[11] Patent Number: 5,409,022
[45] Date of Patent: Apr. 25, 1995

[54] APPARATUS WITH DENTOPROPHYLACTIC CLEANING TOOTHPICKS AND METHOD FOR MANUFACTURING THE SAME

[76] Inventor: Jorge V. Elias, Avenida Insurgentes Sur 505, Suite 502, Colonia Napoles, Mexico, 03810

[21] Appl. No.: 135,898

[22] Filed: Oct. 13, 1993

[30] Foreign Application Priority Data

Oct. 13, 1992 [MX] Mexico .................................... 925872

[51] Int. Cl.⁶ .............................................. A61C 15/00
[52] U.S. Cl. ...................... 132/328; 132/76.2
[58] Field of Search ............ 132/73.5, 75.3, 75.6, 132/76.2, 321, 328, 329

[56] References Cited

U.S. PATENT DOCUMENTS

| | | | |
|---|---|---|---|
| 63,102 | 3/1867 | Russ | 132/76.2 |
| 86,637 | 2/1869 | Bowser | 132/321 |
| 714,901 | 12/1902 | Hills | 132/328 |
| 869,175 | 10/1907 | Gorut | 132/328 |
| 1,240,485 | 9/1917 | Potter | 132/76.2 |
| 1,268,558 | 6/1918 | Faix | 132/76.2 |
| 1,678,609 | 7/1928 | Spanier | 132/328 |
| 2,749,924 | 6/1956 | Polincovsky | 132/76.2 |
| 3,825,961 | 7/1974 | Klein | 132/76.2 |

FOREIGN PATENT DOCUMENTS 9305726 4/1993 WIPO .................. 132/321

*Primary Examiner*—John G. Weiss
*Attorney, Agent, or Firm*—Pennie & Edmonds

[57] ABSTRACT

An apparatus with dentoprophylactic cleaning toothpicks for removing food residues and/or plaque build-ups encrusted between the front and back teeth. The apparatus has a sandwich shaped case, and three toothpick members mounted in the case for pivoting inward and outward of the case.

10 Claims, 3 Drawing Sheets

5,409,022

APPARATUS WITH DENTOPROPHYLACTIC CLEANING TOOTHPICKS AND METHOD FOR MANUFACTURING THE SAME

FIELD OF THE INVENTION

The present invention is aimed at dentoprophylactic cleaning devices and at methods for producing the same and more particularly with an apparatus with dentoprophylactic cleaning toothpicks and with a method for manufacturing said apparatus.

BACKGROUND OF THE INVENTION

At present, there are a variety of dental cleaning devices, such as toothbrushes, toothpicks, floss, etc. They are disposable and, in long run, costly. There are also special instruments for removing plaque. Generally speaking, they are used by dentists. A person who wants the plaque removed and to have his or hers front and back teeth cleaned, has to visit the dentist. This is very costly and requires a great deal of time.

Related to disadvantages of the previously mentioned techniques, as well as many not pointed out, the inventor of the present invention did innumerable studies, tests and experiments, leading him to design an apparatus with dentoprophylactic cleaning toothpicks as well as a method for manufacturing said apparatus.

SUMMARY OF THE INVENTION

The present invention completely overcomes the disadvantages of previous techniques and affords numerous advantages. This is extremely important in the particular area of engineering dealing with this invention.

The apparatus with dentoprophylactic cleaning toothpicks is extremely small, light, compact, durable, and easy to carry, be it in a pants pocket, purse, etc. Anyone can work it, anywhere, anytime.

PREFERRED EMBODIMENT OF THE INVENTION

Figures 1, 2:
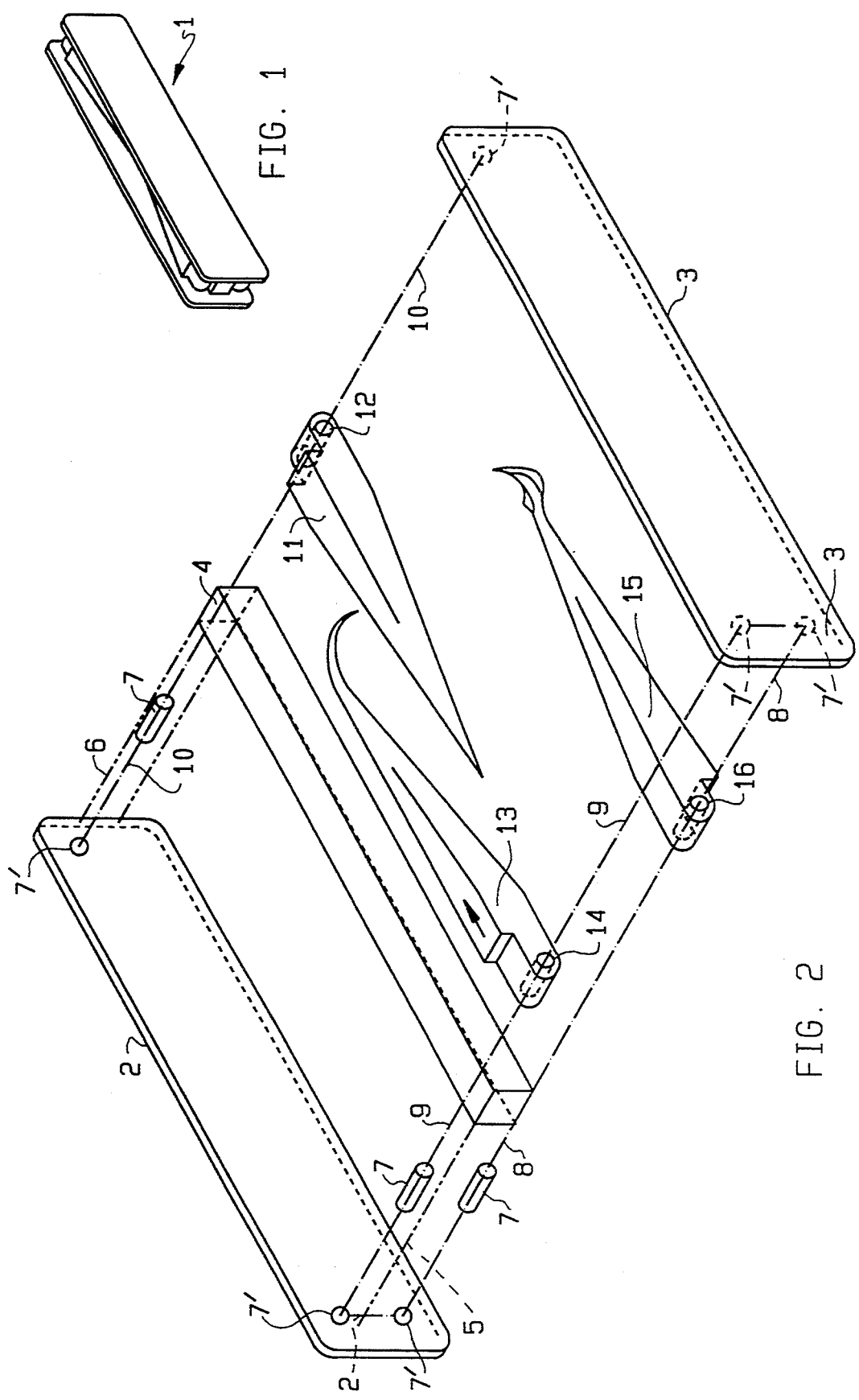
FIG. 1 is a perspective view of the apparatus with dentoprophylactic cleaning toothpicks of the invention.
FIG. 2 is a perspective and exploded view of the apparatus of FIG. 1.

With reference to the drawings, the preferred embodiment of the apparatus with dentoprophylactic toothpicks consists of a rectangular-sandwich shaped case 1, similar to the well-known pocketknife. The case consists of top and bottom sections, a rectangular first section 2 and a rectangular second section 3, made out of a hard material, such as stamped polished stainless steel. An elongated, rectangular tubular section 4, is made of a hard material, such as cut and polished stainless steel. The elongated, rectangular tubular section 4 is placed between the side sections 2 and 3 and extends parallel along their inner faces, touching and joining them. The position of the elongated, rectangular tubular section 4 divides both rectangular side sections 2 and 3 in two equal halves, making upper and lower portions of the case 1. Dotted lines 5 and 6 are used to show the alignment between the rectangular tubular portion 4 with sections 2 and 3. There are also three small cylindrical pins 7 parallel to each other aligned along dot and dash lines 8, 9 and 10 and perpendicular to both rectangular side sections 2 and 3 and the rectangular tubular section 4, as this divides the faces of the rectangular sections. The three small cylindrical pins 7 are made of a hard material, such as cut stainless steel. Two of these small cylindrical pins 7 are placed parallel to each other, a first along the lower dot and dash line 8, in relation to dotted line 5 of the case 1, between the rectangular side section 2 and the rectangular side section 3, and a second on upper dot and dash line 9, in relation to dotted line 5, between the rectangular side section 2 and the rectangular side section 3. The remaining third small cylindrical pin 7 is placed on the dot and dash line 10, in relation to dotted line 6 of the case 1, between the rectangular side section 2 and rectangular side section 3.

Figure 3:
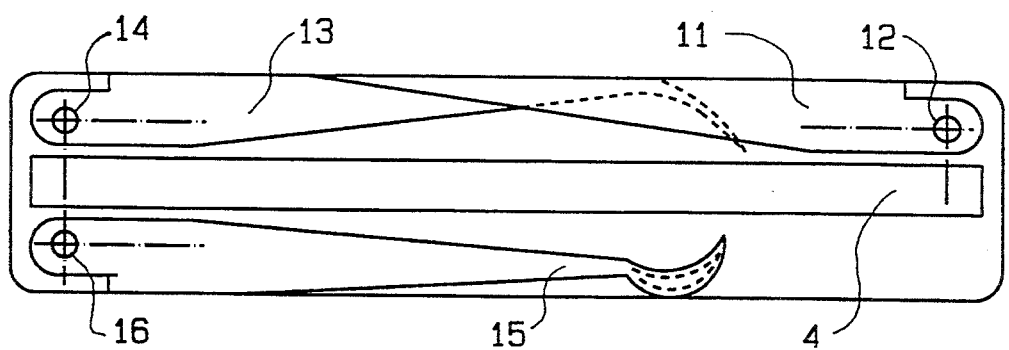
FIG. 3 is a lengthwise front view of the apparatus of FIG. 1.
Figure 4:
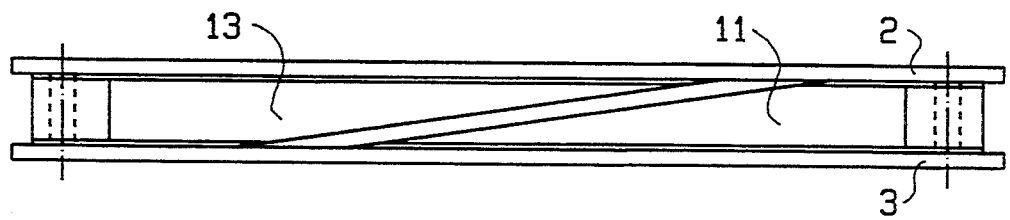
FIG. 4 is a top plan view of the FIG. 3.
Figure 5:
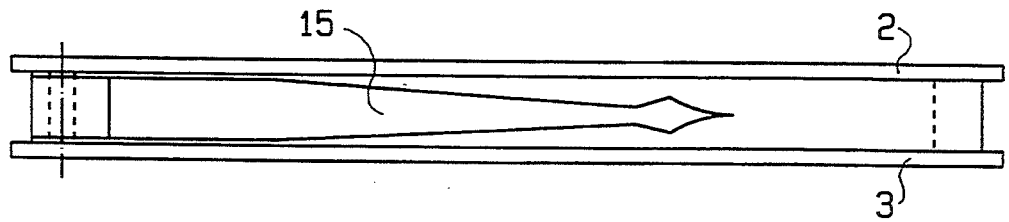
FIG. 5 is a bottom plan view of the lower edge of FIG. 3.
Figure 6:
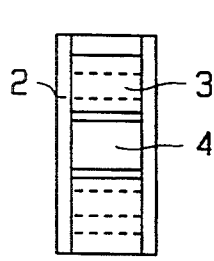
FIG. 6 is a side elevational view of FIG. 3.
Figure 7:
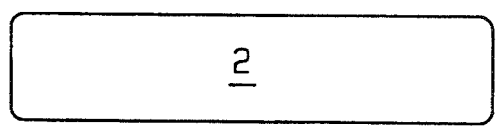
FIG. 7 is a top plan view of a side rectangular surface of the apparatus of FIG. 1.
Figure 9:
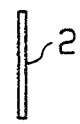
FIG. 9 is an end elevational view of FIG. 7.
Figure 8:
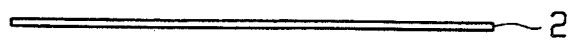
FIG. 8 is a side elevational view of FIG. 7.
Figure 10:
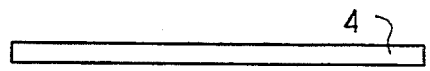
FIG. 10 is a side elevational view of a rectangular section of the apparatus of FIG. 1 thereof.
Figure 11:
FIG. 11 is an end elevational view of FIG. 10.
Figure 12:
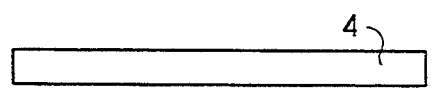
FIG. 12 is a front view of FIG. 10.
Figure 13:
FIGS. 13 and 14 are sectional views of a small cylindrical pin of the apparatus of FIG. 1.
Figure 14:
Figure 15:
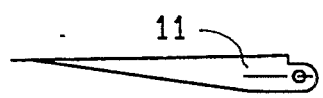
FIG. 15 is a side elevational view of a dentoprophylactic cleaning toothpick of the apparatus of FIG. 1.
Figure 16:
FIG. 16 is an end elevational view of the toothpick of FIG. 15.
Figure 17:
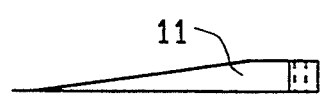
FIG. 17 is a top plan view of the toothpick of FIG. 15.
Figure 18:
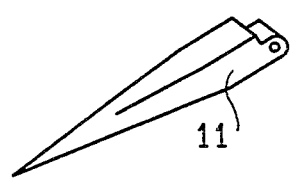
FIG. 18 is a perspective view of the cleaning toothpick of FIG. 15.
Figure 19:
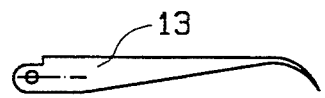
FIG. 19 is a side view of another dentoprophylactic cleaning toothpick of the apparatus of FIG. 1.
Figure 20:
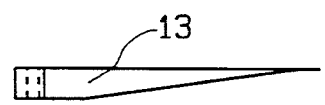
FIG. 20 is a top plan view of the toothpick of FIG. 19.
Figure 21:
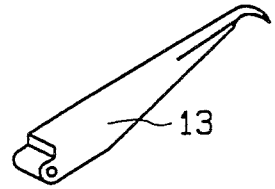
FIG. 21 is a perspective view of the toothpick of FIG. 19.
Figure 22:
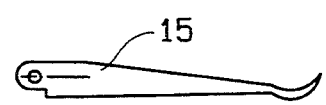
FIG. 22 is a side elevational view of still another dentoprophylactic cleaning toothpick of the apparatus of FIG. 1.
Figure 23:
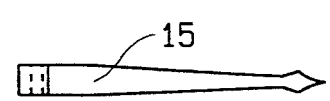
FIG. 23 is a top plan view of the cleaning toothpick of FIG. 22.
Figure 24:
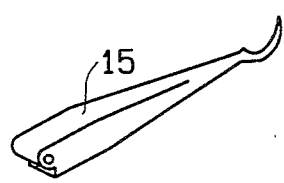
FIG. 24 is a perspective view of the toothpick of FIG. 22.

A first toothpick 11, made of hard injection molded nylon, is joined to the case by means of the third pin 7 which is fitted in the hole 12. The pin extends between the rectangular side section 2 and the rectangular side section 3, close and parallel to the upper surface of the rectangular section 4. It is thus located in the upper portion of the case 1, as shown in FIG. 3. The toothpick 11 is an elongated piece ending in a taper. It can be pivoted inward or outward of the case 1 and is used, among other things, to remove food residue between front and back teeth.

A second toothpick 13, made of hard injection-molded nylon, is joined to the case by means of the second pin 7 which is fitted in the hole 14 of the toothpick. The toothpick 13 is positioned between the rectangular side section 2 and the rectangular side section 3, close and parallel to the upper surface of the rectangular tubular section 4. As with the toothpick 11, it is located in the upper portion of case 1. Toothpick 12 is an elongated piece with a curved hook at its end. It can be pivoted inward or outward of the case 1 and it is used as a complement to toothpick 11. Because of its curved tapered point, toothpick 13 is used to remove food residues from between the front and back teeth portion more easily and efficiently.

The third toothpick 15 is made of molded stainless steel, coming to polished and tempered tapered point. It is joined to the case by means of the first pin 7 which is fitted in a hole 16 of the toothpick. Toothpick 15 is positioned between the rectangular side section 2 and the rectangular side section 3, near and parallel to rectangular section 4 in the lower portion of case 1. Toothpick 15 is an elongated piece ending at a top triangular shape with a tapered point at its end, and it can be pivoted inward or outward of the case 1. The pins 7 are joined to the rectangular side sections 2 and 3 by means of corresponding small notches 7' in said sections.

In its preferred embodiment, the method for manufacturing the apparatus with dentoprophylactic cleaning toothpicks, consists of the following steps: I) cut a pair of stamped and polished sheets of stainless steel, shaping a pair of rectangular sections 2 and 3 side sections, according to predetermined thickness, width and length; II) cut a polished stainless steel rectangular tubular section 4, according to predetermined thickness, width and length; III) cut three small cylindrical stainless steel pins 7, according to predetermined diameter and length; IV) provide a first dentoprophylactic cleaning toothpick 11 made of injection-molded nylon; V) provide a second dentoprophylactic cleaning toothpick 13 made of injection-molded nylon; VI) provide a third dentoprophylactic cleaning toothpick (15) made of polished and tempered molded stainless steel with a top ending in a polished and tempered tapered point; VII) place the rectangular, tubular section 4 on the side section 2 perpendicular and parallel along to rectangular section 2 and locate it one half the distance between the upper and lower edges of the sides 2 and 3 as shown in FIG. 3; VIII) connect the three small cylindrical pins 7 into rectangular section 2 or 3 by means of the three small notches 7', IX) install toothpick 11, with a pin 7 in hole 8, in the notch 7' where dot and dash line 10 touches, in perpendicular relation, the rectangular section 2 or 3; X) install toothpick 13, with a pin 7 in hole 14, in the notch 7' where dot and dash line 9 touches, in perpendicular relation, the rectangular section 2 or 3; XI) install toothpick 15, with a pin 7 in hole 16, in the notch 7' where dot and dash line 8 touches, in perpendicular relation, the rectangular section 2 or 3; XII) test that the toothpicks 11 and 13 are placed in opposite and complementary relative position, being at the relative upper portion of the case and toothpick 15 being at the relative lower portion of case, as divided by rectangular tubular section 4; XIII) join the rectangular sections or sheets 2 and 3 securing the free ends of pins 7 by means of the three free corresponding small notches 7' in one of them, thereby making the case 1.

When a user of the apparatus with dentoprophylactic toothpicks wants to remove food residues from between his or her front and back teeth, he/she pulls and rotates outward the dentoprophylactic cleaning toothpick 11 approximately 180°, introducing it into his/her mouth and picking in and removing out the food residues from between the teeth. Then, the user cleans or washes toothpick 11, rotating it in once again approximately 180°, thereby returning it to its original position into the case.

If the user wants to remove food residue lodged further in, that is, in the inner interdental part of his/her front and back teeth, he/she unfolds the dentoprophylactic cleaning toothpick 13 approximately 180° outwardly and introduces it into his/her mouth, extracting the food residues from the inner interdental part of the front and back teeth. Then, he/she cleans or washes the toothpick 13 and folds it at once again approximately 180°, inward leaving the toothpick 13 in its original position.

Should the user want to remove the plaque from both the inner and outer surfaces of his/her front and back teeth, he/she folds the dentoprophylactic cleaning toothpick 15 outwardly approximately 180°, introducing it into his/her mouth and scrapping the plaque from the teeth until completely removed. Next, he/she cleans or washes the toothpick 15 and folds it approximately 180° in the opposite direction, returning the toothpick 15 to its original position in the case 1.

It is clear that experts in the field could make many changes and variations in this invention without deviating from its spirit and the scope of the invention as set forth in the claims below.

I claim:

1. Apparatus with dentoprophylactic cleaning toothpicks for removing food residues and plaque from front and back teeth, said apparatus comprising:
   a) a rectangular sandwich shaped case constituted of a first side section, a second side section and a rectangular tubular section placed between the side sections, parallel to both and dividing the case internally along two inner faces of the side sections into an upper portion and a lower portion;
   b) a first, a second and a third pin extending parallel to each other, the first and the second of said pins being placed parallel to each other and respectively below and above the rectangular tubular section and perpendicular to both of said side sections, at one end of the case and the third pin being placed parallel to said first and second pins at the other end of the case and in a parallel and complementary opposite position to the second pin;
   c) a first toothpick joined by means of the third pin to both of said side sections in said upper portion of the case parallel and close to the rectangular tubular section;
   d) a second toothpick joined by means of the second pin to both of said side sections in said upper portion of the case, parallel and close to the rectangular tubular section; and
   e) a third toothpick joined by means of the first pin to both of said side sections in the lower portion of the case, parallel and close to rectangular tubular section.

2. An apparatus with dentoprophylactic cleaning toothpicks, according to claim 1, wherein:
   a) the two side sections are rectangular laminates, made of stamped and polished hard material;
   b) the elongated, rectangular and tubular section is made of a cut and polished hard material;
   c) the first, second and third pins are of a cut hard material;
   d) the side sections as well as the tubular section are of predetermined width, thickness and length and the first, second and third pins are of predetermined length and diameter.

3. Apparatus with dentoprophylactic cleaning toothpicks, according to claim 1, wherein:
   a) the first toothpick is of hard injection molded nylon material having an elongated shape ending in a point for removing food residues lodged between the front and back teeth, said first toothpick being mounted on said third pin for folding inward and outward of said case.

4. Apparatus with dentoprophylactic toothpicks, according to claim 1, wherein:
   a) the second toothpick is of hard injection-molded nylon material having an elongated shape ending in a curved point for serving as a complement to the function of the first toothpick to remove food residues from the interdental part of the teeth easily and efficiently, said second toothpick being mounted on said second pin for folding inward and outward of said case.

5. Apparatus with dentoprohylactic cleaning toothpicks, according to claim 1, wherein:
   a) the third toothpick is of stainless steel, with a molded, polished and tempered point and having an elongated shape ending in a triangular configuration coming to said point for removing plaque buildups encrusted between the front and back teeth, said third toothpick being mounted on said first pin for folding inward and outward of the case.

6. Method for manufacturing an apparatus with dentoprophylactic cleaning toothpicks, consisting of the following steps:
   a) cutting a pair of side sections from hard material, of predetermined thickness, width and length;
   b) cutting a polished rectangular tubular section from hard material, of predetermined thickness, width and length;
   c) cutting a first, a second and a third small cylindrical pin from a hard material, of predetermined diameter and length;
   d) providing a first dentoprophylactic cleaning toothpick from a first material;
   e) providing a second dentoprophylactic cleaning toothpick from a second material;
   f) providing a third dentoprophylactic cleaning toothpick from a third material;
   g) placing the stilized rectangular tubular section parallel and perpendicular to the side sections, at one half the distance between and parallel along of both major sides of the side sections;
   h) placing the first, second and the third small cylindrical pins into three small corresponding notches in one of the side sections;
   i) installing the first dentoprophylactic cleaning toothpick by means of placing a pin fixed at said one of said side sections into a corresponding hole in the toothpick, and locating it at a first position;
   j) installing the second dentoprophylactic cleaning toothpick by means of placing a pin fixed at said one of said side sections into a corresponding hole of the toothpick, and locating it at a second position;
   k) installing the third dentoprophylactic cleaning toothpick by means of placing a pin fixed at said one of said side sections into a corresponding hole of the toothpick, and locating it at a third position; and
   l) joining the side sections by means of inserting the three small cylindrical pins in the three small notches of the remaining side section, thereby forming the case.

7. Method for manufacturing an apparatus with dentoprophylactic cleaning toothpicks, according to claim 6, wherein:
   a) the two side sections are made of rectangular laminates and stamped and polished;
   b) the portion is made of an elongated, tubular rectangular piece made of a cut, polished hard material; and
   c) the first, second and third small cylindrical pins are made of cut, polished hard material.

8. Method for manufacturing an apparatus with dentoprophylactic cleaning toothpicks, according to claim 6, wherein:
   a) the first toothpick is made of hard injection molded nylon material as an elongated piece ending in a tapered point, and is mounted in said case for pivoting inward or outward of the case.

9. Method for manufacturing an apparatus with dentoprophylactic cleaning toothpicks, according to claim 6, wherein:
   a) the second toothpick is made of hard, injection molded nylon material as an elongated piece ending in a curved tapered point, and is mounted in said case for pivoting inward or outward of the case.

10. Method for manufacturing an apparatus with dentoprophylactic cleaning toothpicks, according to claim 6, wherein:
    a) the third toothpick is made of molded stainless steel ending in a point, polished and tempered, with an elongated shape ending in a triangular configuration coming to said point, and is mounted in said case for pivoting inward or outward of the case.

* * * * *